(12) United States Patent
Ta

(10) Patent No.: US 8,834,554 B2
(45) Date of Patent: Sep. 16, 2014

(54) INTRAVASCULAR STENT

(75) Inventor: Diem Uyen Ta, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 825 days.

(21) Appl. No.: 11/507,852

(22) Filed: Aug. 22, 2006

(65) Prior Publication Data
US 2008/0086190 A1    Apr. 10, 2008

(51) Int. Cl.
*A61F 2/82* (2013.01)
*A61F 2/915* (2013.01)

(52) U.S. Cl.
CPC ....... *A61F 2/915* (2013.01); *A61F 2002/91516* (2013.01); *A61F 2002/91575* (2013.01); *A61F 2250/0067* (2013.01); *A61F 2002/91558* (2013.01); *A61F 2250/0036* (2013.01); *A61F 2002/91508* (2013.01); *A61F 2002/91541* (2013.01); *A61F 2250/0035* (2013.01); *A61F 2250/0032* (2013.01); *A61F 2250/0018* (2013.01); *A61F 2250/0098* (2013.01)
USPC ...................................... 623/1.15

(58) Field of Classification Search
None
See application file for complete search history.

(56) References Cited

U.S. PATENT DOCUMENTS

| | | | |
|---|---|---|---|
| 2,978,787 A | 4/1961 | Leibig | |
| 2,990,605 A | 7/1961 | Densyk | |
| 3,029,819 A | 4/1962 | Starks | |
| 3,096,560 A | 7/1963 | Liebig | |
| 3,142,067 A | 7/1964 | Liebig | |
| 3,657,744 A | 4/1972 | Ersek | |
| 3,908,662 A | 9/1975 | Razgulov et al. | |
| 3,945,052 A | 3/1976 | Liebig | |
| 4,041,931 A | 8/1977 | Elliott et al. | |
| 4,047,252 A | 9/1977 | Liebig et al. | |
| 4,061,134 A | 12/1977 | Samuels et al. | |
| 4,108,161 A | 8/1978 | Samuels et al. | |
| 4,140,126 A | 2/1979 | Choudhury | |
| 4,193,137 A | 3/1980 | Heck | |
| 4,202,349 A | 5/1980 | Jones | |
| 4,214,587 A | 7/1980 | Sakura, Jr. | |
| 4,517,687 A | 5/1985 | Liebig et al. | |
| 4,560,374 A | 12/1985 | Hammerslag | |
| 4,562,596 A | 1/1986 | Kornberg | |
| 4,577,631 A | 3/1986 | Kreamer | |
| 4,617,932 A | 10/1986 | Kornberg | |
| 4,652,263 A | 3/1987 | Herweck et al. | |

(Continued)

FOREIGN PATENT DOCUMENTS

DE   91 02 312 U1   6/1992
DE   91 13 978      9/2000

(Continued)

OTHER PUBLICATIONS

Lawrence, David D., Jr., M.D., et al. *Percutaneous Endovascular Graft: Experimental Evaluation*, Radiology, vol. 163, No. 2, pp. 357-360 (1987).

(Continued)

*Primary Examiner* — Thomas J Sweet
*Assistant Examiner* — Rebecca Preston
(74) *Attorney, Agent, or Firm* — Fulwider Patton LLP

(57) ABSTRACT

An expandable stent for implanting in a body lumen, such as a coronary artery, peripheral artery, or other body lumen. In one aspect, the stent includes a butterfly pattern to which connecting links are attached. In another aspect, the stent embodies a non-directional structure.

16 Claims, 11 Drawing Sheets

(56) References Cited

U.S. PATENT DOCUMENTS

| | | | |
|---|---|---|---|
| 6,159,238 | A | 12/2000 | Killion |
| 6,165,195 | A | 12/2000 | Wilson et al. |
| 6,183,509 | B1 | 2/2001 | Dibie |
| 6,203,568 | B1 | 3/2001 | Lombardi et al. |
| 6,210,429 | B1 | 4/2001 | Vardi et al. |
| 6,221,098 | B1 | 4/2001 | Wilson et al. |
| 6,254,593 | B1 | 7/2001 | Wilson |
| 6,258,116 | B1 | 7/2001 | Hojeibane |
| 6,264,682 | B1 | 7/2001 | Wilson et al. |
| 6,290,673 | B1 | 9/2001 | Shanley |
| 6,325,826 | B1 | 12/2001 | Vardi |
| 6,346,089 | B1 | 2/2002 | Dibie |
| 6,358,274 | B1 | 3/2002 | Thompson |
| 6,361,555 | B1 | 3/2002 | Wilson |
| 6,478,816 | B1* | 11/2002 | Kveen et al. ............... 623/1.15 |
| 6,613,080 | B1* | 9/2003 | Lootz ............................ 623/1.15 |
| 6,626,935 | B1* | 9/2003 | Ainsworth et al. .......... 623/1.15 |
| 6,629,994 | B2* | 10/2003 | Gomez et al. ............... 623/1.15 |
| 6,776,794 | B1* | 8/2004 | Hong et al. .................. 623/1.15 |
| 6,805,707 | B1* | 10/2004 | Hong et al. .................. 623/1.16 |
| 6,805,898 | B1 | 10/2004 | Wu et al. |
| 7,090,694 | B1 | 8/2006 | Morris et al. |
| 7,862,607 | B2* | 1/2011 | McDermott et al. ......... 623/1.16 |
| 2001/0029397 | A1 | 10/2001 | Thompson |
| 2001/0037137 | A1 | 11/2001 | Vardi et al. |
| 2001/0049548 | A1 | 12/2001 | Vardi et al. |
| 2001/0056297 | A1 | 12/2001 | Hojeibane |
| 2002/0058989 | A1 | 5/2002 | Chen et al. |
| 2002/0198593 | A1 | 12/2002 | Gomez et al. |
| 2003/0036793 | A1 | 2/2003 | Richter et al. |
| 2003/0097169 | A1 | 5/2003 | Brucker et al. |
| 2003/0125802 | A1* | 7/2003 | Callol et al. ................. 623/1.35 |
| 2003/0139796 | A1 | 7/2003 | Sequin et al. |
| 2003/0139803 | A1 | 7/2003 | Sequin et al. |
| 2003/0167083 | A1 | 9/2003 | Lashinski et al. |
| 2003/0195606 | A1 | 10/2003 | Davidson et al. |
| 2004/0044400 | A1 | 3/2004 | Cheng et al. |
| 2004/0073290 | A1* | 4/2004 | Chouinard .................... 623/1.15 |
| 2004/0127977 | A1 | 7/2004 | Shanley |
| 2004/0220663 | A1* | 11/2004 | Rivelli, Jr. .................... 623/1.22 |
| 2004/0230292 | A1* | 11/2004 | Moore ........................... 623/1.15 |
| 2004/0230293 | A1 | 11/2004 | Yip et al. |
| 2004/0243218 | A1 | 12/2004 | Schaeffer |
| 2005/0043782 | A1 | 2/2005 | Gomez et al. |
| 2005/0159807 | A1* | 7/2005 | Bales et al. ................... 623/1.15 |
| 2006/0020322 | A1* | 1/2006 | Leynov et al. ............... 623/1.15 |
| 2006/0030930 | A1* | 2/2006 | Burgermeister et al. .... 623/1.15 |
| 2006/0036312 | A1 | 2/2006 | Tomonto |
| 2006/0100695 | A1 | 5/2006 | Peacock III et al. |
| 2008/0009932 | A1* | 1/2008 | Ta et al. ........................ 623/1.11 |
| 2008/0051876 | A1 | 2/2008 | Ta |
| 2008/0086190 | A1 | 4/2008 | Ta |

FOREIGN PATENT DOCUMENTS

| | | |
|---|---|---|
| EP | 0 461 791 A1 | 12/1991 |
| EP | 0 466 518 A3 | 1/1992 |
| EP | 0 747 020 A2 | 12/1996 |
| EP | 0 804 907 A2 | 11/1997 |
| EP | 0 897 700 A1 | 2/1999 |
| EP | 0 904 745 A2 | 3/1999 |
| EP | 1277440 A1 | 1/2002 |
| EP | 1236445 A2 | 9/2002 |
| FR | 2673843 A1 | 9/1992 |
| FR | 2737969 A1 | 2/1997 |
| JP | 2003724 A | 1/1990 |
| JP | 2002102358 A | 4/2002 |
| SU | 1217402 A | 3/1986 |
| SU | 1318235 A1 | 6/1987 |
| SU | 1389778 A2 | 4/1988 |
| SU | 1457921 A1 | 2/1989 |
| SU | 1482714 A2 | 5/1989 |
| WO | 95/16406 A1 | 6/1995 |
| WO | WO 95/21592 A1 | 8/1995 |
| WO | WO 96/23455 A1 | 8/1996 |
| WO | WO 96/24306 A1 | 8/1996 |
| WO | WO 96/24308 A1 | 8/1996 |
| WO | WO 96/34580 A1 | 11/1996 |
| WO | WO 97/07752 A1 | 3/1997 |
| WO | WO 97/15346 A1 | 5/1997 |
| WO | WO 97/16217 A1 | 5/1997 |
| WO | WO 97/41803 A1 | 11/1997 |
| WO | WO 97/45073 A1 | 12/1997 |
| WO | WO 98/19628 A1 | 5/1998 |
| WO | WO 98/22159 A2 | 5/1998 |
| WO | WO 98/36709 A1 | 8/1998 |
| WO | WO 99/04726 A1 | 2/1999 |
| WO | WO 99/15108 A2 | 4/1999 |
| WO | WO 00/07523 A1 | 2/2000 |
| WO | WO 99/62710 A | 10/2000 |
| WO | WO 01/21095 A2 | 3/2001 |
| WO | WO 92/15824 A2 | 2/2002 |
| WO | WO 02/068012 A1 | 9/2002 |

OTHER PUBLICATIONS

Yoshioka, Tesuya, et al., *Self-Expanding Endovascular Graft: An Experimental Study in Dogs*, Radiology, vol. 170, pp. 673-676 (1989).

Mirich, David, M.D., et al., *Percutaneously Placed Endovascular Grafts for Aortic Aneurysms: Feasibility Study*, Radiology, vol. 170, No. 3, Part 2, pp. 1033-1037 (1989).

Parodi, J.C., M.D., et al., *Transfemoral Intraluminal Graft Implantation for Abdominal Aortic Aneurysms*, Annals of Vascular Surgery, vol. 5, No. 6, pp. 491-499 (1991).

Chuter, Timothy A.M., et al., *Transfemoral Endovascular Aortic Graft Placement*, Journal of Vascular Surgery, pp. 185-196 (Aug. 1993).

Bard XT Carina Bifurcate Stent (Brochure) (Undated).

U.S. Appl. No. 11/841,291, filed Aug. 20, 2007; Amendment/RCE filed on Dec. 21, 2011.

* cited by examiner

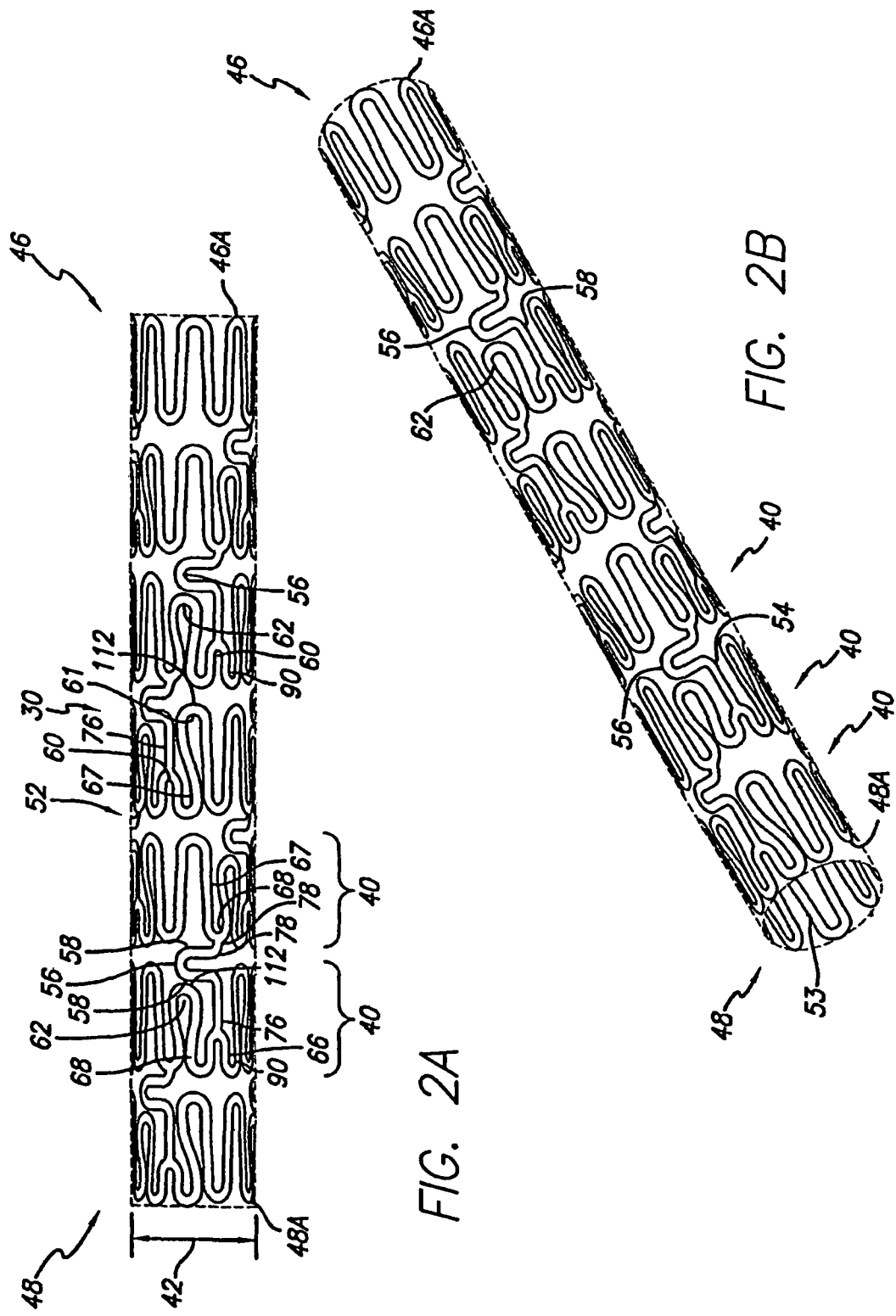

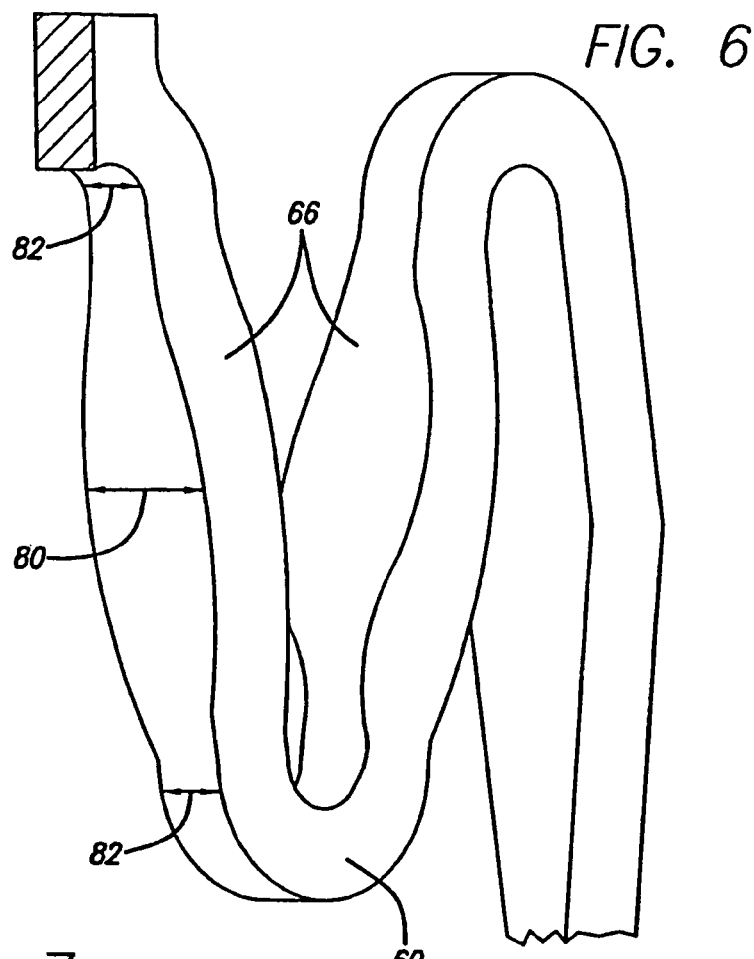
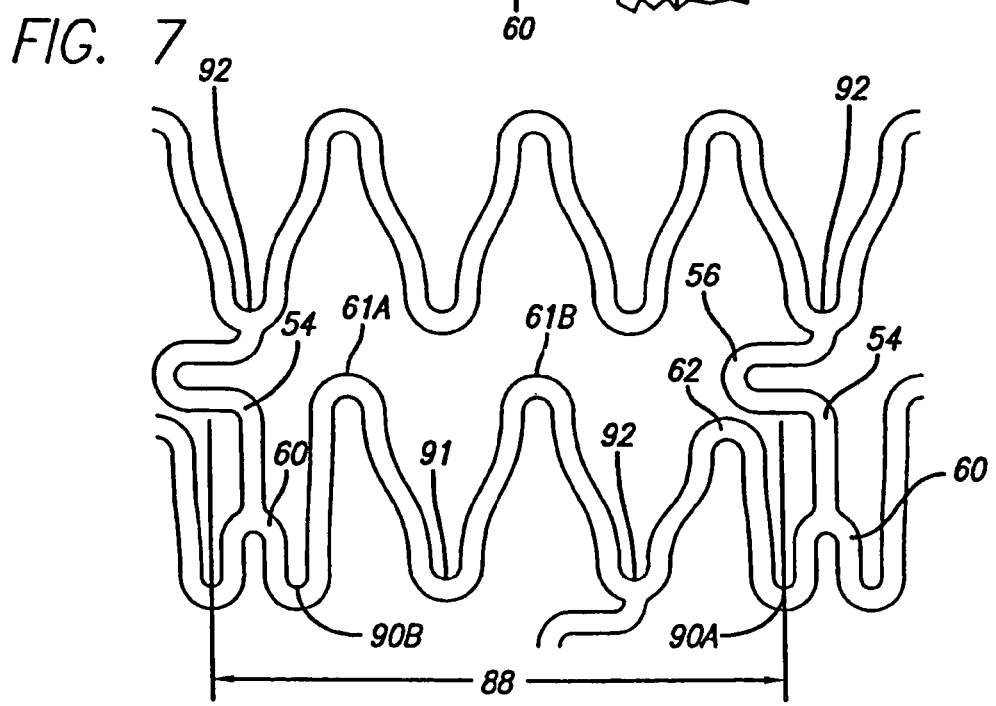

INTRAVASCULAR STENT

BACKGROUND OF THE INVENTION

The invention relates to vascular repair devices and, in particular, to intravascular stents including rings with substructure reducing strain and enhancing flexibility as well as to stents having non-directional structural patterns.

Stents are generally tubular-shaped devices which function to hold open a segment of a blood vessel. They also are suitable for use to support and hold back a dissected arterial lining that can occlude the fluid passageway. That is, whether self-expanding or expandable using force, stents are delivered within vasculature in a radially compressed configuration and then implanted at an interventional site while assuming a radially expanded configuration. At present, there are numerous commercial stents being marketed throughout the world. For example, some known prior art stents have multiplex cylindrical rings connected by one or more links. While some of these stents are flexible and have the appropriate radial rigidity needed to hold open a blood vessel, there typically is a tradeoff between flexibility and radial strength and the ability to tightly compress or crimp the stent onto a catheter so that it does not move relatively to the catheter or dislodge prematurely prior to controlled implantation at an interventional site.

As stated, various conventional stents include a plurality of rings connected by links. In certain stents, the rings include a plurality of peaks and valleys connected by bar arms. When these rings are positioned in phase relatively to one another, W-crests and Y-crests are formed at the points of connection between the links and rings. Once a stent embodying this structure is implanted at an interventional site, a significant amount of strain is placed upon the peaks and valleys. In fact, the link can become angulated or twisted upon stent expansion resulting in an overall twisted stent configuration. Such a twisted stent configuration can suffer from inadequate vessel wall apposition and thus, may not perform optimally in holding a vessel open. Further, the degree of twisting often cannot be predicted due to manufacturing and material variability which consequently limits the reliability of stent function.

Other factors also contribute to the unpredictability of stent performance. That is, conventional stents embody a pattern of links and rings which can be characterized as directional in configuration. A typical stent include a pattern of adjacently arranged rings which extend the length of a stent and includes a first end which differs from that of a second end of the stent. Due to this directional structure, such a stent must be placed upon a catheter in a particular direction so that when it is deployed and implanted within vasculature, the stent will be arranged as contemplated to achieve expected performance. Unfortunately, conventional stents embodying directional structure can be placed on a catheter incorrectly due to operator error, and it is difficult to either identify this error or correct it during a surgical procedure.

Accordingly, what has been needed and heretofore unavailable is a stent including structure which provides desired flexibility without compromising radial strength and reduces unwanted stresses and twisting. Moreover, there is a need for a stent which addresses problems associated with directional stents. The present invention satisfies these and other needs.

SUMMARY OF THE INVENTION

The present invention is directed to an intravascular stent including structure enhancing flexibility without compromising radial strength and minimizing twisting and inherent stresses. The present invention is also directed towards a stent incorporating a non-directional pattern of rings and links.

In one aspect, the invention includes a flexible intravascular stent for use in a body lumen, comprising a plurality of cylindrical rings aligned along a common longitudinal axis and interconnected to form the stent, each cylindrical ring having a first delivery diameter and a second larger implanted diameter. Each cylindrical ring includes an open W or butterfly pattern to which one end of a link between adjacent rings is connected. Further, each ring includes a plurality of first peaks, second peaks, and third peaks, adjacent third peaks defining the butterfly pattern. Each of the peaks has a height and an apex, the first peaks being taller than the second peaks, and the second peaks being taller than the third peaks. Described in another way, each cylindrical ring has a plurality of first valleys, second valleys, and third valleys, adjacent third valleys forming the butterfly pattern. Moreover, each of the valleys has a depth and an apex, the first valleys being deeper than the second valleys, and the second valleys being deeper than the third valleys.

At least one link attaches each cylindrical ring to an adjacent cylindrical ring. The links can include an undulation having a curved portion extending transverse to the stent longitudinal axis toward the second peak. Additionally, the curved portion of the undulating link can be longitudinally aligned with the second peak. Also, each undulating link can include an arm that is straight and parallel to the longitudinal axis of the stent and which is circumferentially offset from the second peak.

The invention further contemplates peaks and valleys having a different radii and/or heights than other or adjacent peaks and valleys. In still another aspect of the invention, at least a portion of the links or cylindrical rings can have a variable thickness configuration and/or a variable width.

Still another aspect of the invention is directed towards a non-directional stent. Such a stent is not required to be mounted onto a stent delivery system in a particular proximal-distal orientation. The configuration of peaks and valleys at a proximal end of the stent is generally a mirror image of the configuration of peaks and valleys at the distal end. Both the proximal end and the distal end cylindrical rings may include various combinations of tall peaks, intermediate peaks, short peaks, deep valleys, intermediate valleys, and shallow valleys. Further, the non-directional stent can include the open W or butterfly pattern. In one embodiment, at least two of the open W or butterfly pattern configurations face in opposite directions from each other along the length of the stent. In addition, it is contemplated that not all of the curved portions of the undulating links face in the same direction in the non-directional stent. Because the proximal and distal ends of the stent are generally mirror image configurations or a rotated mirror image of the opposite end of the stent, and the configuration of peaks and valleys of the rings is reversed at one or more points along the length of the stent, the non-directional stent may be mounted onto a stent delivery system in either direction.

Other features and advantages of the present invention will become more apparent from the following detailed description of the invention, when taken in conjunction with the accompanying exemplary drawings.

BRIEF DESCRIPTION OF THE DRAWINGS

The invention is herein described, by way of example only, with reference to the accompanying drawings, wherein:

FIG. 2A is a plan view of a portion of the stent of FIG. 1 forming a radially compressed cylindrical configuration.

FIG. 2B is a perspective view of a portion of the stent of FIG. 2A.

FIG. 6 is an enlarged cutaway perspective view of a portion of an embodiment of a stent having struts with varying radial thickness.

FIG. 7 is an enlarged plan view of a portion of the stent of FIG. 1.

DETAILED DESCRIPTION OF THE PREFERRED EMBODIMENTS

Figure 1:
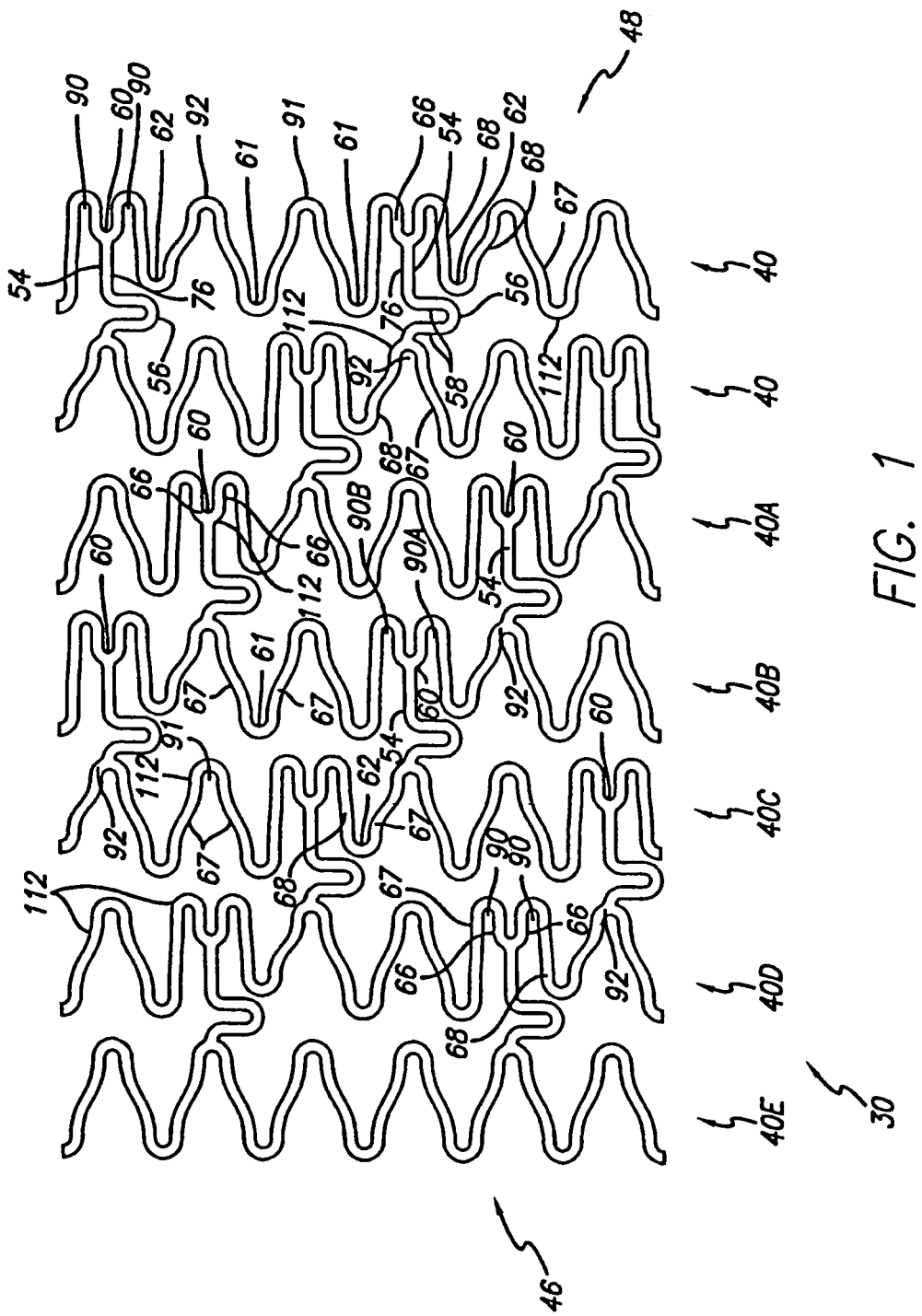
FIG. 1 is a plan view of a portion of a flattened stent of one embodiment of the invention which illustrates a pattern of rings and links.

Referring to the drawings, which are provided for purposes of illustration and by way of example but not limitation, the present invention is illustrated in FIGS. 1-9B.

Turning now to FIG. 1, an exemplary stent 30 of the present invention is shown in a flattened condition so that the pattern can be clearly viewed, even though the stent is in a cylindrical form in use, such as shown in FIGS. 2A-B. The stent is typically formed from a tubular member, however it can be formed from a flat sheet such as shown in FIG. 1 and rolled into a cylindrical configuration.

Figure 3A:
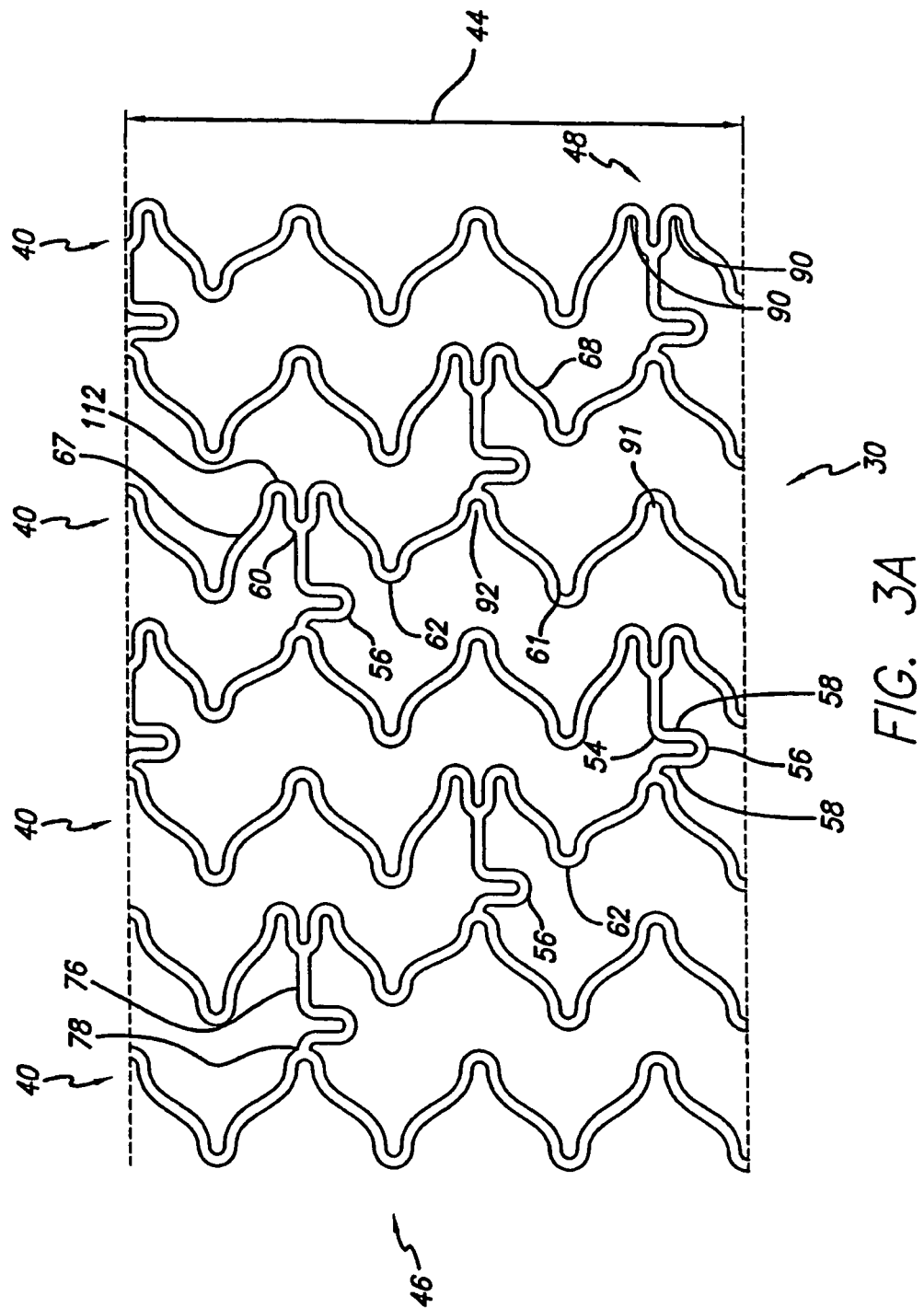
FIG. 3A is a plan view of a portion of the stent of FIG. 1 in a flattened configuration and illustrating the rings and links in an expanded configuration.
Figure 3B:
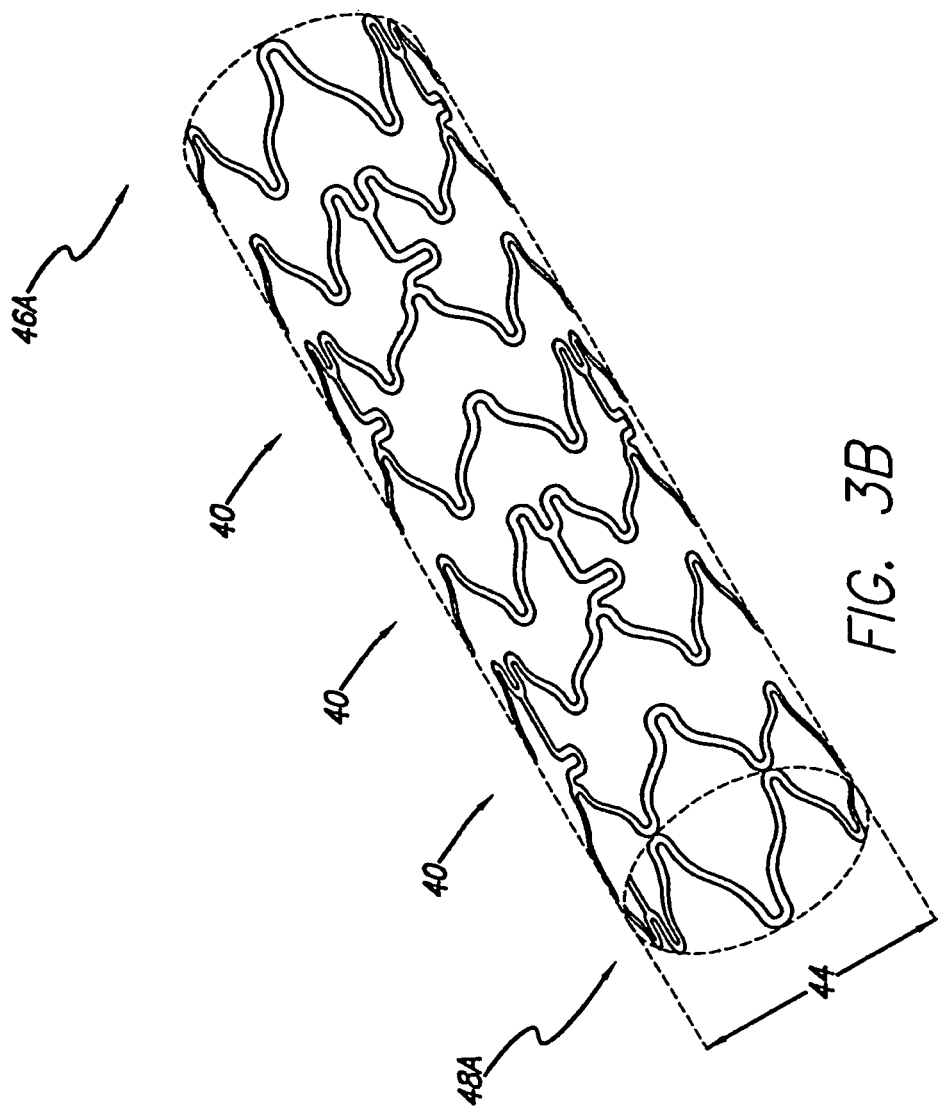
FIG. 3B is a perspective view of a portion of the stent of FIG. 1 in a cylindrical configuration and illustrating the rings and links in an expanded configuration.

As shown in FIGS. 1-3B, stent 30 is made up of a plurality of cylindrical rings 40 which extend circumferentially around the stent. It is to be recognized that there may be fewer or more cylindrical rings than is shown in the illustrated drawings. The rings are aligned along a common longitudinal axis and interconnected by links 54 to form the stent. The links 54 can be generally straight members (See FIG. 5) or can include one or more curves or turns as shown in the figures. Moreover, links with undulation can be configured at all locations or any selected locations along the stent. The stent has a delivery diameter 42 (FIG. 2A), and expands to an implanted diameter 44 (FIGS. 3A and 3B). The stent has a proximal end 46 and a distal end 48. Typically, since the stent is contemplated to be laser cut from a tube, there are no discreet parts.

Referring specifically to FIG. 2B, each cylindrical ring includes a cylindrical outer wall surface 52 which defines the outermost surface of the stent and a cylindrical inner wall surface 53 which defines the innermost surface of the stent. The links 54 connect one cylindrical ring 40 to an adjacent cylindrical ring 40. To prevent links 54 from compromising the longitudinal flexibility of the stent, a curved portion 56 is incorporated into link 54. This curved portion 56 is connected to one or more substantially straight portions 58 wherein the straight portions 58 are substantially perpendicular to the longitudinal axis of the stent. Thus, as the stent is being delivered through a tortuous vessel, such as a coronary artery, the curved portions 56 and straight portions 58 of the undulating links will permit the stent to flex in the longitudinal direction which substantially enhances delivery of the stent to the target site. The number of bends and straight portions in a link can be increased or decreased from that shown to achieve different flexibility constructions. In one embodiment (not shown), it is contemplated that the links can comprise a plurality of curved portions and straight portions 58. With the straight portions being substantially perpendicular to the stent longitudinal axis, the link 54 acts much like a hinge at the curved portion 56 to provide flexibility in both crimped and expanded states. The number of links 54 can be adjusted to vary the longitudinal flexibility in the crimped and expanded states of a stent.

The stent 30 further can be described as having rings including a plurality of alternative peaks and valleys. The peaks and valleys can have similar or different sizes. In one embodiment, the rings can include one or more open W or butterfly patterns of struts to which links between adjacent rings are connected. Accordingly, the rings can include a plurality of short peaks 60, tall peaks 61, intermediate peaks 62, shallow valleys 90, deep valleys 91, and intermediate valleys 92. The peaks and valleys are formed from various length struts and apices 112. In one embodiment, the struts include short struts 66, long struts 67, and intermediate struts 68. The lengths of these struts can be varied to achieve a desired expansion diameter. As shown, each open W or butterfly pattern is defined by one short peak 60, two short struts 66, one long strut 67 and one intermediate strut 68. The struts can be either curved or straight depending upon a particular application. Also, as shown, each peak has a height, the tall peaks being taller than the intermediate peaks, and the intermediate peaks being taller than the short peaks. Additionally, each valley has a depth, the deep valleys being deeper than the intermediate valleys, and the intermediate valleys being deeper than the shallow valleys. In other embodiments, a greater range in the types of heights of peaks and/or a greater range in the types of depths of valleys may be included.

Additionally, in one aspect, the stent 30 can further include one or more Y patterns of struts. With reference to FIG. 2B, the Y pattern is defined by one intermediate valley 92, one long strut 67, and one intermediate strut 68.

It is also contemplated that a stent of the present invention can further include at least one additional peak (not shown) having a different height than the short peak, the tall peak, and the intermediate peak. Also, the stent can further include at least one additional valley (not shown) having a different depth than the shallow valley, the intermediate valley, and the deep valley. For example, one embodiment may have four different height peaks and four different depth valleys. Moreover, the number of peaks and valleys can vary in number for each ring depending upon the application. Thus, for example, if the stent is to be implanted in a coronary artery, a lesser number of peaks and valleys are required than if the stent is implanted in a peripheral artery, which has a larger diameter than a coronary artery. Moreover, the number of peaks and valleys can be adjusted to vary the expansion diameter. Furthermore, the order or juxta-positioning of various sized peaks and valleys can be varied within a ring or from one ring to another, and the various peaks and valleys of adjacent rings can be aligned or offset from each other. It is to be understood that the definition of an open W pattern should not be limited but generally should imply the presence of a plurality of apexes including both one or more peaks and valleys of different heights and depths.

In one particular embodiment, illustrated as example in the peaks 60, 61 and 62 of each ring 40 are oriented towards the proximal end 46, and the valleys 90, 91 and 92 of each ring 40 are oriented towards the distal end 48. These rings can be positioned in phase relatively to one another, meaning that the peaks of one ring are separated from the peaks of the adjacent ring by one ring width plus the spacing between the rings. Likewise, the valleys of one ring are separated from the valleys of the adjacent ring by one ring width plus the spacing between the rings.

As stated, it may be desirable under certain circumstances to position the peaks so that they are out of phase (not shown), that is, the apexes of the peaks of one ring are circumferentially offset from the apexes of the peaks of an adjacent ring. Positioning the peaks, valleys, and links in this manner, provides a stent having desirable expansion capabilities, high radial strength, a high degree of flexibility, and sufficient wall coverage to support a vessel.

As can be seen, for example, in FIGS. 1-2B, curved portion 56, straight portions 58 have been designed such that when crimped, intermediate peak 62 would nest in the space just distal to the curved portion 56 and straight portions 58. This nesting allows the stent 30 to be tightly crimped onto a delivery system to achieve a low crimped OD.

Referring to FIGS. 2A-2B, the crimping or compressing process, circumferentially moves the undulating link 54 along with its curved portion 56 closer to the intermediate peak 62. Although the various stent struts, curved portions, links, and peaks and valleys may contact each other when the stent is crimped or compressed, it may be desirable to avoid the overlapping of struts 66, 67, 68, apexes 112, and links 54.

Figure 4:
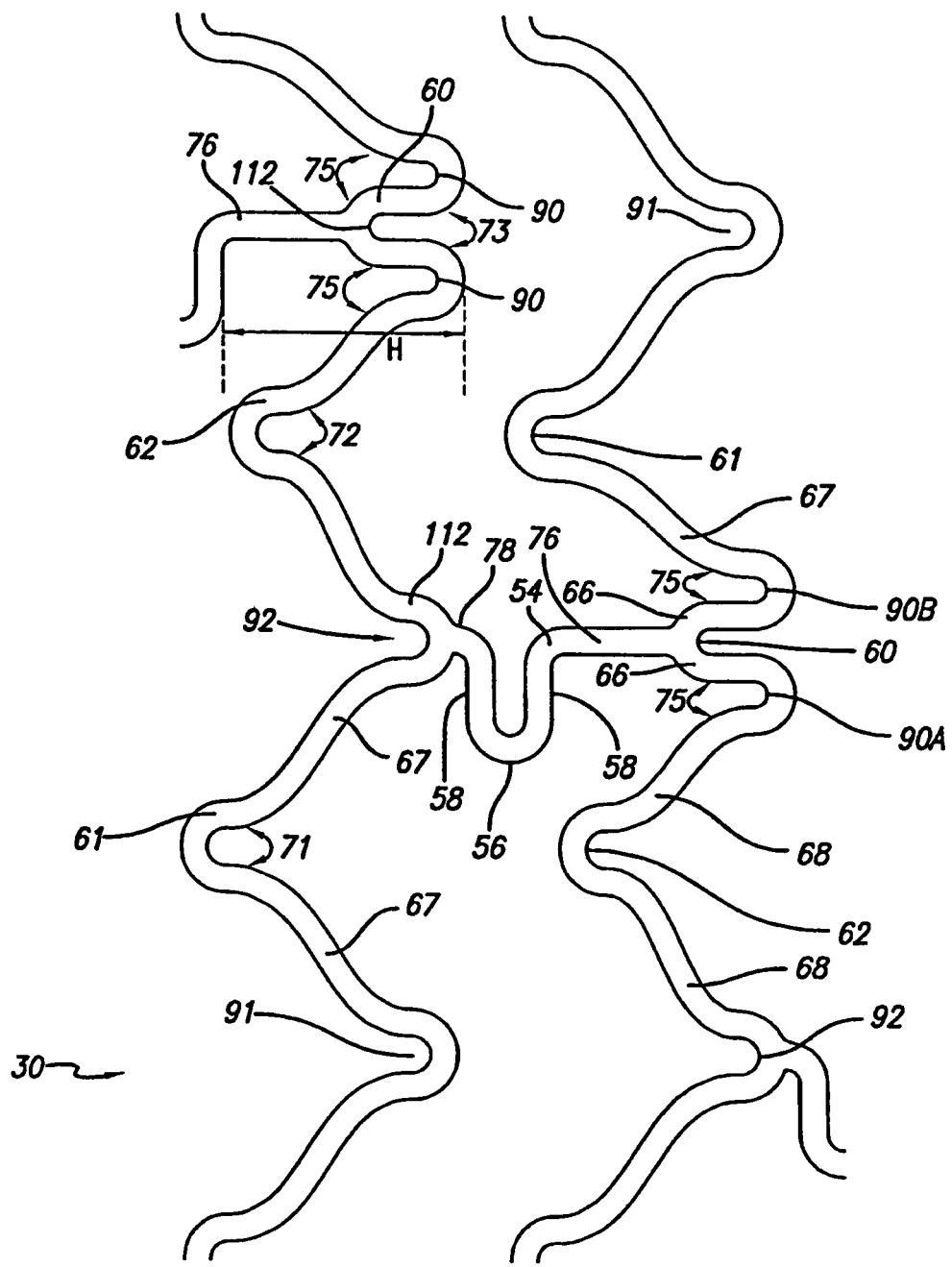
FIG. 4 is an enlarged plan view of a portion of the stent of FIG. 1.

Referring now to FIG. 4, in one embodiment, an arm 76 of the link 54 is attached to the apex 112 of a short peak 60. The length of the arm may vary in different embodiments. The other end 78 of the link 54 is attached to the apex 112 of an intermediate valley 92. Notably, in this embodiment, combined height "H" of the short peak 60 and the arm 76 is longer than the length of the intermediate peak 62 when the stent is in both the compressed and expanded configurations. This allows the stent to be tightly compressed onto a catheter or other stent delivery device, and such structure can be employed to avoid overlapping between the undulating link 54 and the intermediate peak 62. In addition, the circumferential positioning of the intermediate peak 62 and tall peaks 61 can be varied to avoid the intermediate peak 62 and tall peak 61 from touching arm 78 of link 54.

Due to the intricate patterns as disclosed in FIGS. 1-4, the rate of expansion of the various portions of the stent can vary. Accordingly, one aspect of the invention provides for different radii of curvature at various apexes 112 so that the stent will expand evenly and uniformly. Referring more specifically now to FIG. 4, first radius 71 which corresponds with tall peak 61 may have a smaller radius of curvature than does second radius 72 which corresponds with intermediate peak 62. Generally, the longer the struts associated with a peak, the more easily that portion of the stent will expand, so that a smaller radius is associated with peaks having two long struts 67. Likewise, for peaks, such as short peak 60, which has struts 66 that are shorter than the struts 67 of tall peak 61, the apex 112 may have a greater radius 73 of curvature which will expand more easily in order to compensate for the stiffer bending moments created by the shorter struts 66. In yet other embodiments, the radii of curvature of the various peaks and various valleys may be adjusted so that the different types of peaks and valleys expand at different tensions rather than expanding uniformly. In addition, the circumferential positioning of the intermediate peak 62 and tall peaks 61 can be varied to achieve uniform expansion.

The radii 75 of the shallow valleys 90 may also be varied to provide uniform stent expansion. Since a shallow valley formed by an intermediate strut 68 and a short strut 66 can have a tendency to expand more slowly as the stent is expanded compared to a shallow valley formed by a long strut 67 and a short strut 66, a greater radius of a curvature may be incorporated into the shallow valley having the intermediate strut 68. Thus, third radius 75 of a first shallow valley 90A may be greater than the fourth radius 75 of a second adjacent shallow valley 90B. By varying the radii of curvature in the shallow valleys, the stent may expand more evenly and compensate for the varying rates of expansion of adjacent portions in a cylindrical ring.

Figure 5:
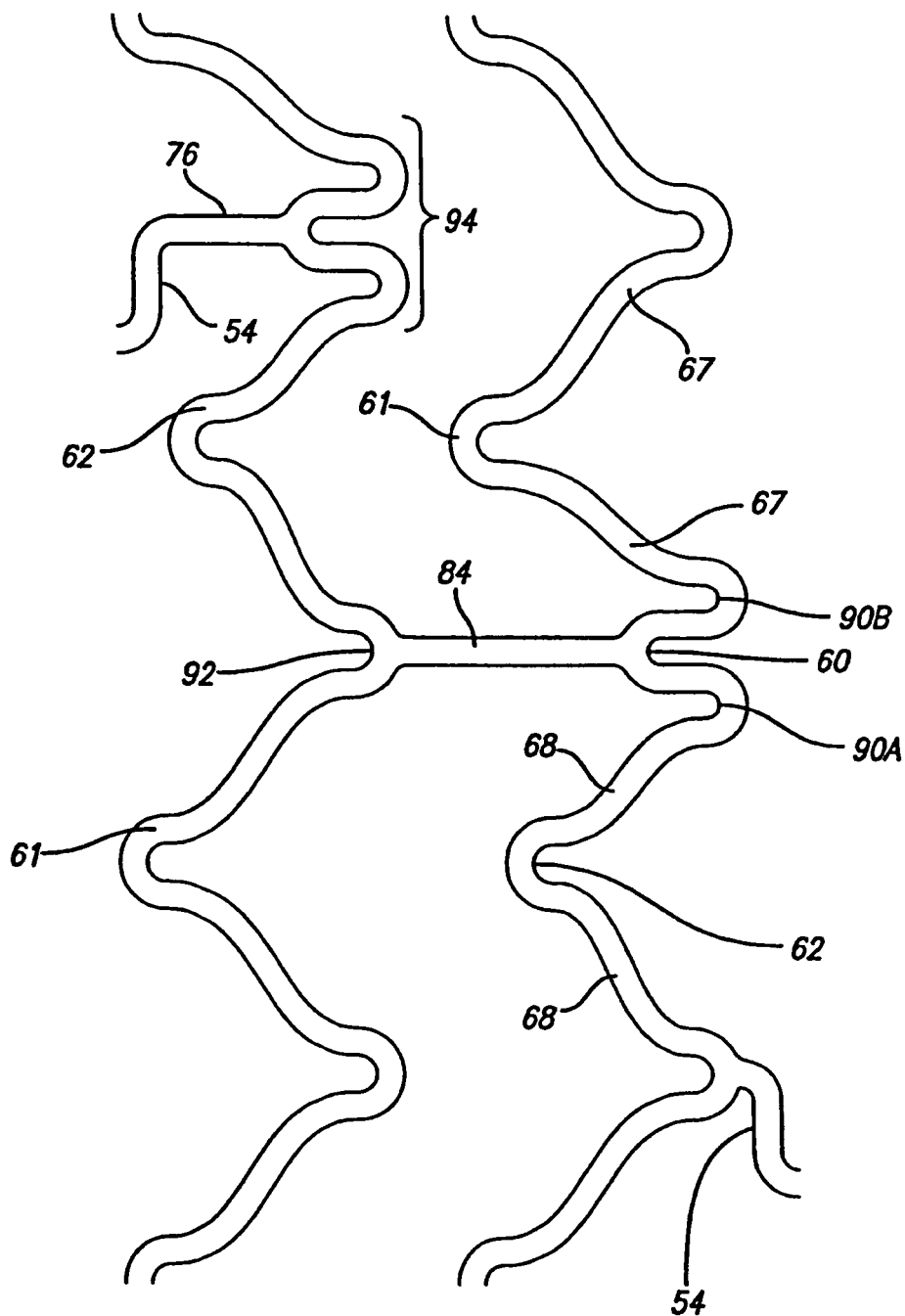
FIG. 5 is an enlarged plan view of a portion of an embodiment of a stent including straight links in an expanded configuration.

Typical stents known in the art undergo a lot of strain as they go from a compressed configuration to an expanded configuration. The strain produced by the expansion of a stent may cause the links to be angulated, resulting in a twisted stent. With reference to FIG. 5, the open W butterfly pattern 94 is shown including two shallow valleys 90 connected with each other by a short peak 60. The butterfly pattern 94 is designed to reduce the strain exerted on the peaks 60, 61, 62, valleys 90, 91, 92, struts 66, 67, 68, and links 54 during expansion of the stent 30. Moreover, the butterfly pattern 94 design facilitates achieving better crimping profiles since the short crest and long crest are positioned further away from the linear link, so during crimping the long crest and short crest have a longer distance to travel before hitting the linear link. It is especially beneficial when the stent is coated with a drug because it prevents or at least minimizes a possibility of coating damage. Moreover, the butterfly W crest increases the stent flexibility since both valleys 90 are two separate components which can move to accommodate any bending when the crimped stent tracks through tortuousity.

As previously stated, it is also a design feature that more or fewer links 54 including curved portions be positioned between adjacent cylindrical rings 40. As shown in FIG. 5, straight links 84 in addition to undulating links 54 may be included to connect adjacent cylindrical rings. The straight links can be employed to provide stability and assist in stent length change, as an adjunct to the undulating links.

Further, the straight links may be employed in various alternative approaches to provide more rigidity in a localized area, such as at the stent ends. For example, it may be desirable to incorporate more straight links between the cylindrical rings at the stent ends 46, 48 (FIG. 2B) than in the interposed rings 40A, 40B, 40C (FIG. 1) of the stent. In fact, in one contemplated embodiment, all links can assume a substantially straight configuration.

In another aspect of the invention, as shown in FIG. 6, the stent 30 is formed so that the various elements of the cylindrical rings 40, including the long struts 67, short struts 66, intermediate struts 68, various peaks 60, 61, 62, various valleys 90, 91, 92, and the undulating links 54, all can be formed so that each has a variable thickness along the stent length. For example, the undulating link 54 may be thicker at the arm 76 portion than at the extension 78 portion of the link. Such structure can reduce deployment pressure while maintaining radial strength. Further, short struts 66, long struts 67, and intermediate struts 68 may vary in thickness (radial thickness) along their length in order to create variable flexibility in the rings. Moreover, in one contemplated approach short peak 60 has short struts 66 that can have radial thick portion 80 in the middle of the struts and radial thin portion 82 near the ends of the struts. As another example (not shown), the ring 40E at the proximal end 46 and/or ring 40 at the distal end 48 of the stent may be thicker radially than the other cylindrical rings 40 of the stent. It is also to be recognized that the proximal end ring 40E can have a unique configuration, one that is different from the remaining rings of the stent 30.

Turning now to FIG. 7, in one contemplated embodiment, at least one cylindrical ring 40 includes a repeating pattern of peaks and valleys. That is, for example, each pattern segment 88 includes in sequence a short peak 60, a shallow valley 90B, a tall peak 61A, a deep valley 91, a tall peak 61B, an intermediate valley 92, an intermediate peak 62, and a shallow valley 90A. The pattern segment may repeat itself as many times as necessary to provide a cylindrical ring of a desired expansion diameter. Also, adjacent cylindrical rings can be connected by one undulating link 54 per pattern segment. For example, an undulating link may connect the short peak 60 of one cylindrical ring to the intermediate valley 92 of an adjacent cylindrical ring. Further, there may be more than one undulating link 54 or straight link 84 (FIG. 5) per pattern segment. In other contemplated embodiments, the links 54, 84 may connect any of the various types of peaks 60, 61, 62 and valleys 90, 91, 92 to any other or same type of peak or valley. Adjacent cylindrical rings can have the same repeating pattern or may have different repeating patterns from each other.

Referring back now to FIG. 1, in one embodiment, the stent of the present invention includes a repeating pattern segment including four peaks and four valleys, and the short peak 60 of a first ring 40A is linked to and longitudinally aligned with the intermediate valley 92 of an adjacent second ring 40B. The short peak 60 of the second ring 40B is linked to and longitudinally aligned with the intermediate valley 92 of an adjacent third ring 40C. In other words, the pattern of the second ring 40B is rotated from the pattern of the first ring 40A, and the pattern of the third ring 40C is further rotated from the pattern of the second ring 40B. This rotational pattern results in the short peaks being longitudinally aligned every third cylindrical ring. Such a three ring longitudinal design may then be repeated as desired to add additional length to a stent. In at least one embodiment, the most proximal end 46A or most distal end 46B of the stent 30 may have a row 40E of undulations having all the same length struts 66, or 67, or 68.

Figure 8A:
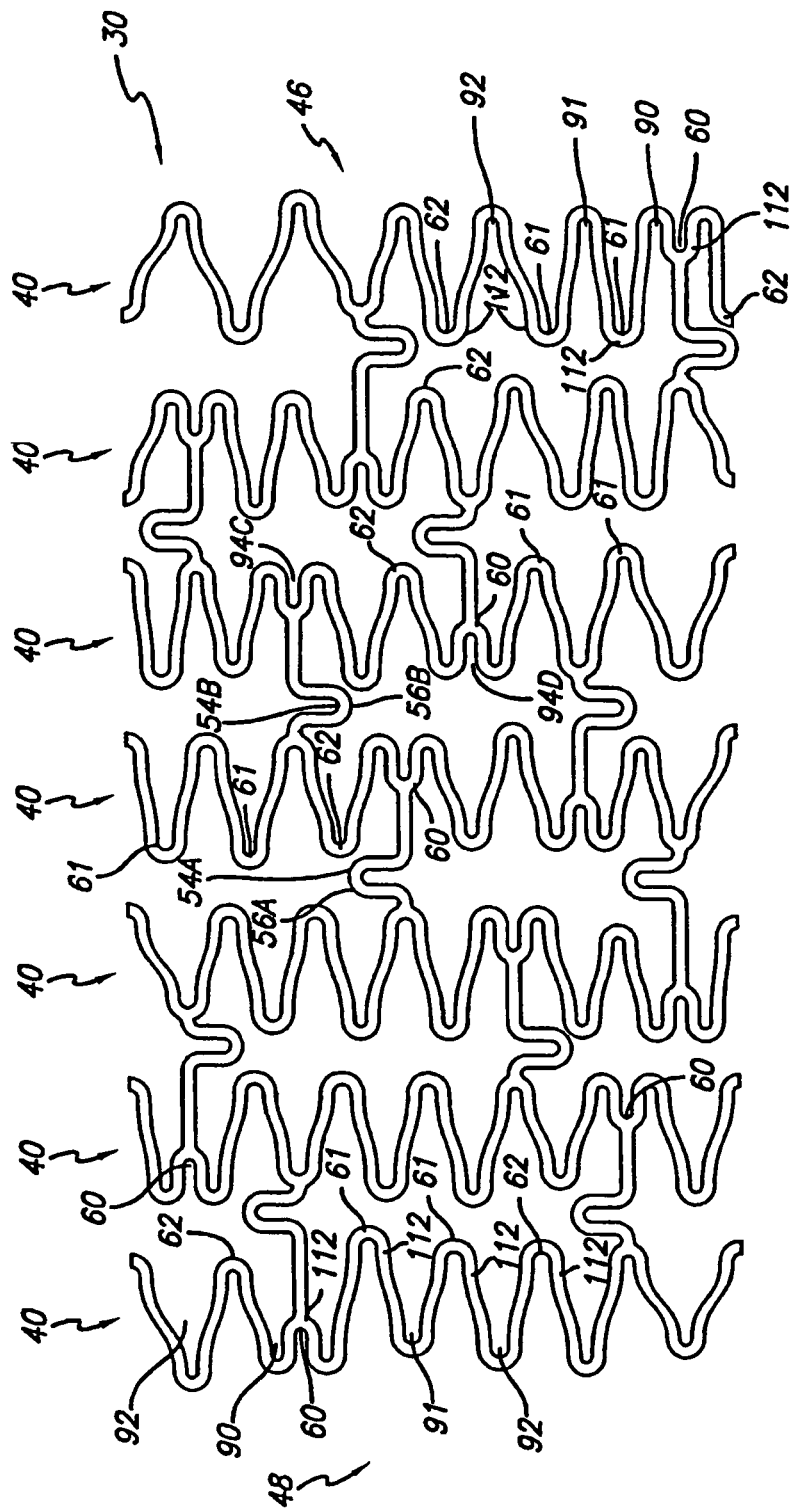
FIG. 8A is a plan view of a portion of one embodiment of a non-directional stent in a flattened configuration.
Figure 8B:
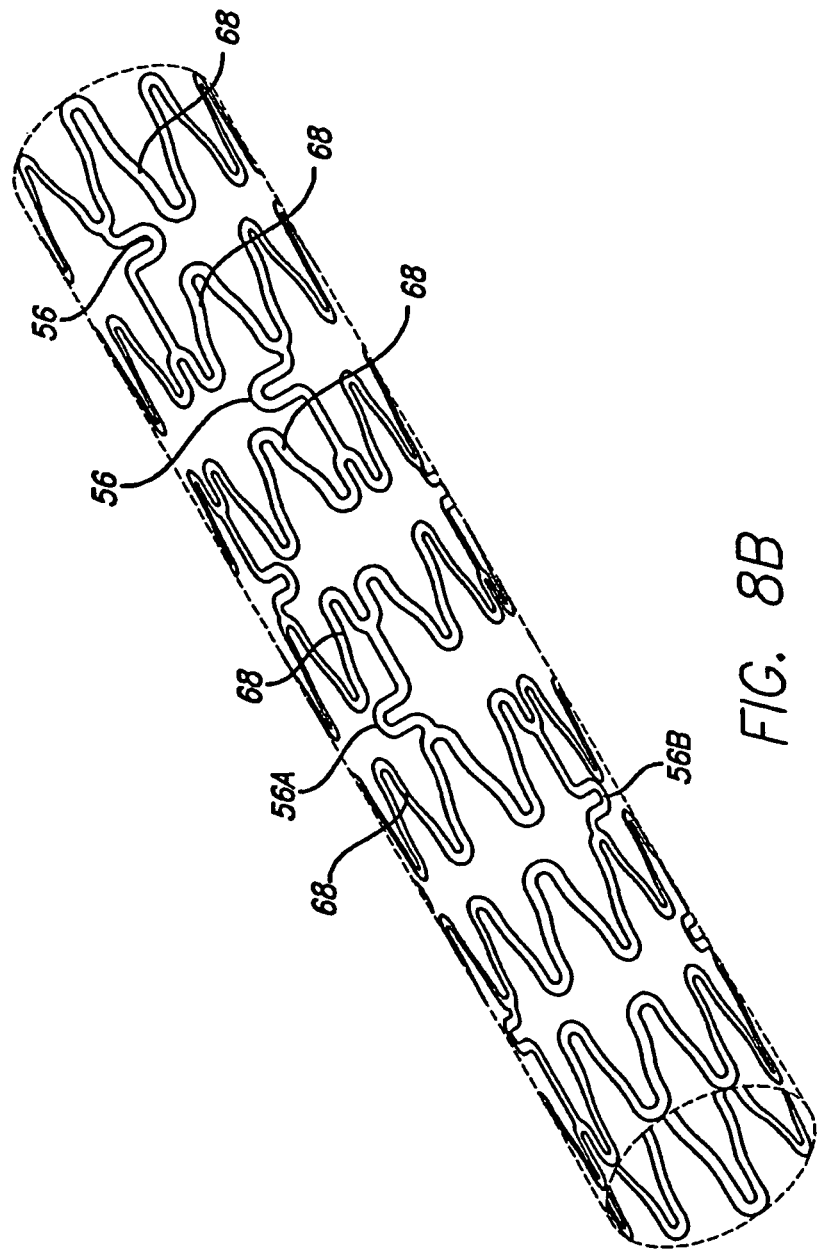
FIG. 8B is a perspective view of a portion of the stent of FIG. 8A in a cylindrical configuration.
Figure 9A:
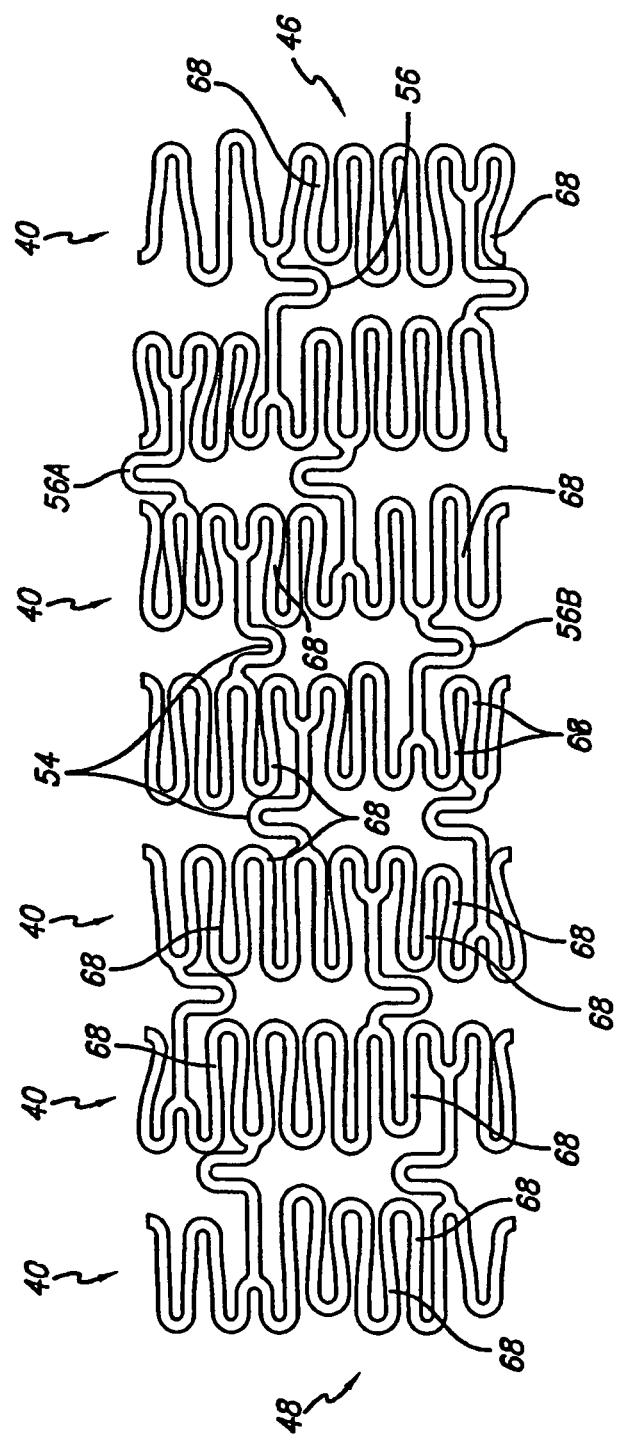
FIG. 9A is a plan view of a portion of the stent of FIG. 8A in a flattened compressed configuration.
Figure 9B:
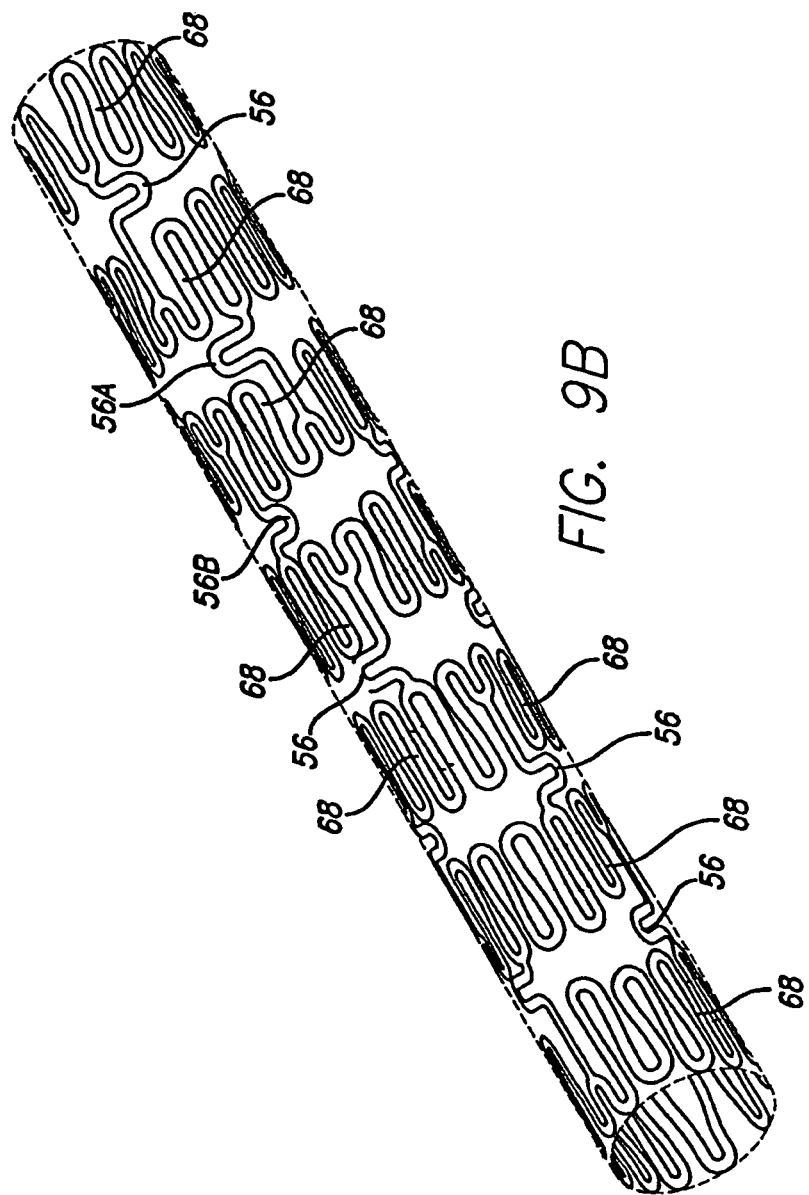
FIG. 9B is a perspective view of a portion of the stent of FIG. 9A forming a radially compressed cylindrical configuration.

Referring now to FIGS. 8A-9B, yet another aspect of the stent 30 is embodied in a non-directional stent. Notably, the non-directional stent may be mounted on a delivery device with either the proximal or distal end of the stent oriented towards the distal end of the delivery device with equal effectiveness. Thus, the non-directional stent may be mounted onto a stent delivery system (not shown), for example a balloon catheter, without it being positioned in a preferred proximal-distal orientation. FIGS. 8A-8B show representative features of a portion of the non-directional stent in an as-manufactured (flat and cylindrical) configuration, and FIGS. 9A-9B show representative features of a portion of the non-directional stent in a compressed configuration (flat and cylindrical).

In one embodiment of the non-directional stent, all of apexes 112 of the peaks 60, 61, 62 on the most proximal end 46 cylindrical ring 40 of the stent 30 point distally and, all of apexes 112 of the peaks 60, 61, 62 on the most distal end 48 cylindrical ring 40 point proximally. Similarly, all of the valleys 90, 91, 92 of the most distal end 48 ring 40 face proximally, and all of the valleys of the most proximal end 46 ring 40 face distally. Stated another way, all of the peaks on the proximal end 46 ring 40 point towards all of the peaks on the distal end 48 ring 40. Additionally, all of the valleys on the proximal end 46 ring 40 point towards all of the valleys on the distal end 48 ring 40.

In a further aspect, along the entire length of the stent, there may be approximately equal numbers of peaks 60, 61, 62 having apexes 112 that point towards the proximal end 46 of the stent 30 and peaks having apexes that point towards the distal end 48 of the stent. There may also be along the entire length of the stent approximately equal numbers of valleys 90, 91, 92 having apexes 112 that point towards the proximal end 46 of the stent 30 and valleys having apexes that point towards the distal end 48 of the stent.

In still another aspect (not shown), it is contemplated that at least some of the intervening rings 40 that are located between the proximal end 46 and the distal end 48 may include peaks 60, 61, 62 having apexes 112 that point proximally, and some of the other rings may include peaks having apexes that point distally. Similarly, at least some of the intervening rings 40 that are located between the proximal end 46 and the distal end 48 may include valleys 90, 91, 92 having apexes 112 that point proximally, and some of the other rings may include valleys having apexes that point distally.

Moreover, in each of the rings 40 of the stent 30 there may be approximately equal number of peaks 60, 61, 62 having apexes 112 that point towards the proximal end 46 of the stent and peaks having apexes that point towards the distal end 48 of the stent. There may also be in each of the rings of the stent approximately equal number of valleys 90, 91, 92 having apexes that point towards the proximal end of the stent and valleys having apexes that point towards the distal end of the stent.

Furthermore, not all of the apexes 112 of the peaks 60, 61, 62 on one ring 40 need to be aligned in the same direction. For example, some of apexes 112 of the peaks 60, 61, 62 on the ring 40 may point distally 48, and some of the apexes of the peaks on the ring 40 may point proximally 46. Also, some of apexes 112 of the valleys 90, 91, 92 on the ring 40 may point distally 48, and some of the apexes of the valleys on the ring 40 may point proximally 46. Additionally, the rings may be rotationally offset from each other or configured to be in-phase.

As illustrated in FIG. 8A, the non-directional stent includes at least two of the butterfly patterns oriented in opposite longitudinal directions from each other. Moreover, in certain approaches, it may be desirable to configure the stent so that the oppositely oriented butterfly pattern may be on the same ring or on different rings. For example, butterfly 94C has an opposite longitudinal orientation from butterfly 94D.

In at least one additional embodiment, not all of the curved portions 56 of the undulating links 54 face in the same orientation in the non-directional stent. For example, as shown in FIGS. 8A-9B, curved portion 56A of undulating link 54A faces in an opposite circumferential direction from curved portion 56B of undulating link 54B.

Furthermore, it is also contemplated that a non-directional stent of the present invention can include both the oppositely oriented butterfly patterns of FIG. 8A as well as undulating links facing in opposite circumferential directions as depicted in FIG. 8B. Moreover, such features can be incorporated into directional stents where desired.

Additionally, in the non-directional stent (See FIGS. 8-9B), the intermediate struts 68 can be configured to remain adjacent to the curved portions 56 of the undulating links 54. Furthermore, the arm 76 of the undulating link 54 is typically connected to a short peak 60 in the various embodiments of the non-directional stent.

The stent 30 of the present invention can be made in many ways. One method of making the stent is to cut a thin-walled tubular member, such as a stainless steel tubing to remove portions of the tubing in the desired pattern for the stent, leaving relatively untouched the portions of the metallic tubing which are to form the stent. The stent also can be made from other metal alloys such as tantalum, nickel-titanium, cobalt-chromium, titanium, shape memory and superelastic alloys, and the nobel metals such as gold or platinum. In accordance with the invention, it is preferred to cut the tubing in the desired pattern by means of a machine-controlled laser as is well known in the art.

Other methods of forming the stent of the present invention can be used, such as using different types of lasers, chemical etching, electric discharge machining, laser cutting a flat sheet and rolling it into a cylinder, and the like, all of which are well known in the art at this time.

The stent of the present invention also can be made from metal alloys other than stainless steel, such as shape memory alloys. Shape memory alloys are well known and include, but are not limited to, nickel-titanium and nickel-titanium-vanadium. Any of the shape memory alloys can be formed into a tube and laser cut in order to form the pattern of the stent of the present invention. As is well known, the shape memory alloys of the stent of the present invention can include the type having superelastic or thermoelastic martensitic transformation or display stress-induced martensite. These types of alloys are well known in the art and need not be further described here.

The present invention stent is also ideally suited for drug delivery (i.e., delivery of a therapeutic agent) since it has a uniform surface area which ensures uniform distribution of drugs. Typically, a polymer containing the drug is coated onto the stent of the type disclosed in U.S. Pat. Nos. 6,824,559 and 6,783,793 which are incorporated herein by reference.

It is contemplated that the stent 30 of the present invention can be mounted on a stent delivery device or system, for example, a balloon catheter (not shown) similar to those known in the prior art. The stent delivery device includes a distal end for mounting of a stent thereon, and a proximal end configured to remain external to a patient's blood vessel. An example of a stent delivery system is disclosed in U.S. Pat. No. 6,629,994 entitled "INTRAVASCULAR STENT" filed Jun. 11, 2001, the entirety of which is incorporated herein by reference. The present invention, however, is not intended to be limited to delivery using the disclosed stent delivery systems but may be used with other stent delivery systems known in the art. The stent may be tightly compressed or crimped on the balloon portion of the catheter and remains tightly crimped on the balloon during delivery through the patient's vascular system. When the balloon is inflated, the stent expands radially outwardly into contact with the body lumen, for example, a coronary artery. When the balloon portion of the catheter is deflated, the catheter system is withdrawn from the patient, and the stent remains implanted in the artery.

Similarly, if the stent of the present invention is made from a self-expanding metal alloy, such as nickel-titanium or the like, the stent may be compressed onto a catheter, and a sheath (not shown) is placed over the stent to hold it in place until the stent is ready to be implanted in the patient. Such sheaths are well known in the art. Once the stent has been positioned at the intended location, the sheath is retracted and the stent self-expands into contact with the wall of the artery. Catheters for delivering self-expanding stents are well known in the art.

It is to be recognized that the invention may be embodied in other forms without departing from the spirit and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention. Accordingly, the scope of the invention is intended to be defined only by reference to the appended claims.

What is claimed:

1. A flexible intravascular stent for use in a body lumen, comprising:
a plurality of cylindrical rings aligned along a common longitudinal axis; and
a plurality of links connecting adjacent cylindrical rings, two or more of the plurality of links being an undulating link, each undulating link having a curved portion extending transverse to the common longitudinal axis and an arm being straight and parallel to the common longitudinal axis;
wherein each cylindrical ring includes an open W-pattern, the open W-pattern being connected to no more than one adjacent ring, each of the cylindrical rings having a plurality of first peaks, second peaks, and third peaks, each of the first, second and third peaks having a height and an apex, the first peaks being taller than the second peaks, and the second peaks being taller than the third peaks along with a plurality of first valleys, second valleys, and third valleys, each of the first, second and third valleys having a depth and an apex, the first valleys being deeper than the second valleys, and the second valleys being deeper than the third valleys, each third peak of at least one of the cylindrical rings being connected to an adjacent cylindrical ring by one of the undulating links and the open W-pattern is formed between one of the first peaks and one of the second peaks.

2. The stent of claim 1, wherein each undulating link further includes at least one substantially straight portion connected to the curved portion, the at least one substantially straight portion being substantially perpendicular to the common longitudinal axis.

3. The stent of claim 2, wherein the at least one substantially straight portion of each undulating link is perpendicular to the common longitudinal axis.

4. The stent of claim 1, wherein the apexes of the first peaks have a first radius, and the apexes of the second peaks have a second radius, the second radius being different than the first radius.

5. The stent of claim 1, wherein each cylindrical ring includes a plurality of a first strut, a second strut, and a third strut, the first struts being longer than the second struts, and the second struts being longer than the third struts.

6. The stent of claim 1, wherein the stent has a proximal end and a distal end and defines a first longitudinal orientation of the apexes of the first, second and third peaks and the apexes of the first, second and third valleys at the proximal end which is generally reversed from a second longitudinal orientation of the apexes of the first, second and third peaks and the apexes of the first, second and third valleys at the distal end.

7. The stent of claim 1, wherein the stent has a proximal end and a distal end and the apex of at least one third peak of one of the cylindrical rings is oriented towards the proximal end of the stent, and the apex of at least one other third peak on another of the cylindrical rings is oriented towards the distal end of the stent.

8. The stent of claim 1, wherein orientations of at least some of the peaks and some of the valleys are longitudinally reversed along a length of the stent, wherein the stent may be effectively mounted onto a stent delivery system in at least two different orientations.

9. The stent of claim 1, wherein a plurality of struts define the rings and each link, at least a portion of one strut having a variable thickness.

10. The stent of claim 1, wherein a plurality of struts define the rings and each link, at least a portion of one strut having a variable width.

11. The stent of claim 1, wherein the open W-pattern includes two short struts connected together to form one of the third peaks having a radius, a first long strut connected to one end of one of the short struts to form one of the first valleys having a radius and a second long strut connected to one end of the other short strut to form one of the second valleys having a radius.

12. The stent of claim 1, wherein each of the first peaks has a smaller radius of curvature than each of the second peaks and each of the second peaks has a smaller radius of curvature than each of the third peaks.

13. A flexible intravascular stent for use in a body lumen, comprising:
a plurality of cylindrical rings aligned along a common longitudinal axis; and
a plurality of links connecting adjacent cylindrical rings;
wherein each cylindrical ring includes an open W-pattern, the open W-pattern being connected to no more than one adjacent ring, each of the cylindrical rings having a plurality of first peaks, second peaks, and third peaks, each of the first, second and third peaks having a height and an apex, the first peaks being taller than the second peaks, and the second peaks being taller than the third peaks along with a plurality of first valleys, second valleys, and third valleys, each of the first, second and third valleys having a depth and an apex, the first valleys being deeper than the second valleys, and the second valleys being deeper than the third valleys, each third peak of at least one of the cylindrical rings being connected to an adjacent cylindrical ring by one of the links and the open W-pattern is formed between one of the first peaks and one of the second peaks and each cylindrical ring includes a plurality of a first strut, a second strut, and a third strut, the first struts being longer than the second struts, and the second struts being longer than the third struts and the open W-pattern is defined by a pair of third struts, one first strut and one second strut.

14. A flexible intravascular stent for use in a body lumen, comprising:
a plurality of cylindrical rings aligned along a common longitudinal axis; and
a plurality of links connecting adjacent cylindrical rings;
wherein each cylindrical ring includes an open W-pattern, the open W-pattern being connected to no more than one adjacent ring, each of the cylindrical rings having a plurality of first peaks, second peaks, and third peaks, each of the first, second and third peaks having a height and an apex, the first peaks being taller than the second peaks, and the second peaks being taller than the third peaks along with a plurality of first valleys, second valleys, and third valleys, each of the first, second and third valleys having a depth and an apex, the first valleys being deeper than the second valleys, and the second valleys being deeper than the third valleys, each third peak of at least one of the cylindrical rings being connected to an adjacent cylindrical ring by one of the links and the open W-pattern is formed between one of the first peaks and one of the second peaks and each cylindrical ring includes a plurality of a first strut, a second strut, and a third strut, the first struts being longer than the second struts, and the second struts being longer than the third struts and at least one of the second valleys includes one of the second struts connected with another of the second struts by one of the apexes.

15. A flexible intravascular stent for use in a body lumen, comprising:
a plurality of cylindrical rings aligned along a common longitudinal axis; and
a plurality of links connecting adjacent cylindrical rings;
wherein each cylindrical ring includes an open W-pattern, the open W-pattern being connected to no more than one adjacent ring, each of the cylindrical rings having a plurality of first peaks, second peaks, and third peaks, each of the first, second and third peaks having a height and an apex, the first peaks being taller than the second peaks, and the second peaks being taller than the third peaks along with a plurality of first valleys, second valleys, and third valleys, each of the first, second and third valleys having a depth and an apex, the first valleys being deeper than the second valleys, and the second valleys being deeper than the third valleys, each third peak of at least one of the cylindrical rings being connected to an adjacent cylindrical ring by one of the links and the open W-pattern is formed between one of the first peaks and one of the second peaks and each cylindrical ring includes a plurality of a first strut, a second strut, and a third strut, the first struts being longer than the second struts, and the second struts being longer than the third struts and at least one of the second struts is of dissimilar length than at least one other of the second struts.

16. A flexible intravascular stent for use in a body lumen, comprising:
a plurality of cylindrical rings aligned along a common longitudinal axis; and
a plurality of links connecting adjacent cylindrical rings;
wherein each cylindrical ring includes an open W-pattern, the open W-pattern being connected to no more than one adjacent ring, each of the cylindrical rings having a plurality of first peaks, second peaks, and third peaks, each of the first, second and third peaks having a height and an apex, the first peaks being taller than the second peaks, and the second peaks being taller than the third peaks along with a plurality of first valleys, second valleys, and third valleys, each of the first, second and third valleys having a depth and an apex, the first valleys being deeper than the second valleys, and the second valleys being deeper than the third valleys, each third peak of at least one of the cylindrical rings being connected to an adjacent cylindrical ring by one of the links and the open W-pattern is formed between one of the first peaks and one of the second peaks and each cylindrical ring includes a plurality of a first strut, a second strut, and a third strut, the first struts being longer than the second struts, and the second struts being longer than the third struts and each of the second peaks includes one of the second struts connected with another of the second struts at the apex which defines that second peak.

* * * * *